United States Patent
Ansermet et al.

(10) Patent No.: US 9,763,056 B2
(45) Date of Patent: Sep. 12, 2017

(54) BLUETOOTH BEACON TRANSMISSION

(71) Applicant: POLAR ELECTRO OY, Kempele (FI)

(72) Inventors: Raphael Ansermet, Neuchatel (CH); Niclas Granqvist, Magenwil (CH); Markku Karjalainen, Kempele (FI)

(73) Assignee: POLAR ELECTRO OY, Kempele (FI)

( * ) Notice: Subject to any disclaimer, the term of this patent is extended or adjusted under 35 U.S.C. 154(b) by 0 days.

(21) Appl. No.: 14/319,754

(22) Filed: Jun. 30, 2014

(65) Prior Publication Data

US 2015/0382150 A1 Dec. 31, 2015

(51) Int. Cl.
*H04W 4/00* (2009.01)
*H04W 4/04* (2009.01)
(Continued)

(52) U.S. Cl.
CPC ............ *H04W 4/04* (2013.01); *A61B 5/002* (2013.01); *A61B 5/112* (2013.01); *A61B 5/1118* (2013.01); *A61B 5/222* (2013.01); *G06Q 10/0639* (2013.01); *G06Q 50/22* (2013.01); *H04B 5/0031* (2013.01); *H04M 1/7253* (2013.01); *H04W 4/008* (2013.01); *A61B 5/02055* (2013.01); *A61B 5/02405* (2013.01); *A61B 5/1112* (2013.01); *A61B 5/1113* (2013.01); *A61B 5/4872* (2013.01); *A61B 5/6898* (2013.01); *A61B 5/7465* (2013.01); *A61B 2503/10* (2013.01); *A61B 2503/12* (2013.01); *A61B 2562/0219* (2013.01); *H04M 2250/02* (2013.01)

(58) Field of Classification Search
CPC ....................................................... H04W 4/008
USPC ...................... 455/41.1, 41.2, 41.3
See application file for complete search history.

(56) References Cited

U.S. PATENT DOCUMENTS 8,630,586 B2 * 1/2014 Dvortsov .............. H04W 12/04
455/41.2
2002/0077060 A1 6/2002 Lehikoinen et al.
(Continued)

FOREIGN PATENT DOCUMENTS

EP 2335563 A1 6/2011
EP 2634652 A1 9/2013
WO WO2014082665 A1 6/2014

OTHER PUBLICATIONS

European Search Report for corresponding European Application No. EP15171325, pp. 1-2 (Oct. 27, 2015).

*Primary Examiner* — Wen Huang
(74) *Attorney, Agent, or Firm* — Hoffman & Baron, LLP

(57) ABSTRACT

There is provided a radio device, comprising: a Bluetooth circuitry configured to generate and advertise a Blue-tooth beacon signal having frame format according to the Bluetooth standard; a proximity communication circuitry configured to receive configuration commands wirelessly from a physically separate user device over a magnetic induction-based proximity communication; and at least one processor and at least one memory including a computer program code, wherein the at least one memory and the computer pro-gram code are configured, with the at least one processor, to cause the radio device to perform operations comprising: reconfiguring at least part of data content of the Bluetooth beacon signal on the basis of the received configuration commands, wherein the data content of the Bluetooth beacon signal is set to comprise at least physical activity related information.

16 Claims, 4 Drawing Sheets

(51) Int. Cl.
  H04B 5/00 (2006.01)
  G06Q 10/06 (2012.01)
  G06Q 50/22 (2012.01)
  H04M 1/725 (2006.01)
  A61B 5/22 (2006.01)
  A61B 5/00 (2006.01)
  A61B 5/0205 (2006.01)
  A61B 5/024 (2006.01)
  A61B 5/11 (2006.01)

(56) References Cited

U.S. PATENT DOCUMENTS

| | | | | |
|---|---|---|---|---|
| 2009/0280745 | A1* | 11/2009 | Granqvist | A61B 5/0002 455/41.3 |
| 2011/0054359 | A1* | 3/2011 | Sazonov | A43B 3/0005 600/595 |
| 2011/0126143 | A1* | 5/2011 | Williams | G06F 3/0488 715/771 |
| 2012/0254934 | A1* | 10/2012 | McBrearty | G06F 19/3481 725/118 |
| 2013/0135115 | A1* | 5/2013 | Johnson | G08C 19/00 340/870.02 |
| 2013/0165044 | A1* | 6/2013 | Xie | H04W 52/0229 455/41.2 |
| 2013/0245966 | A1* | 9/2013 | Burroughs | G06F 19/3481 702/44 |
| 2014/0135593 | A1* | 5/2014 | Jayalth | A61B 5/0022 600/301 |
| 2014/0221160 | A1* | 8/2014 | Hardy | A63B 24/0062 482/8 |
| 2014/0266160 | A1* | 9/2014 | Coza | G01B 7/003 324/207.11 |
| 2014/0357192 | A1* | 12/2014 | Azogui | H04B 7/26 455/41.2 |
| 2015/0281364 | A1* | 10/2015 | Connolly | G06Q 10/10 709/217 |
| 2015/0334548 | A1* | 11/2015 | Liu | H04W 8/005 370/329 |

* cited by examiner

BLUETOOTH BEACON TRANSMISSION

BACKGROUND

The invention relates generally to local transmission. More particularly, the invention relates to sharing data to many users using a Bluetooth beacon transmission.

DESCRIPTION OF THE RELATED ART

It often happens that data needs to be transmitted by a source device to many target devices fast. In such case, pairing with the target devices may be too time consuming. Moreover, often the data that is to be transmitted needs to be adapted to each individual situation.

SUMMARY

The invention is defined by the independent claims.

According to an aspect of the invention, there is provided a computer program product readable by a computer and comprising program instructions which, when loaded into an apparatus, execute any of the embodiments as described in the appended claims.

According to an aspect of the invention, there is provided a computer-readable distribution medium carrying the above-mentioned computer program product.

According to an aspect of the invention, there is provided an apparatus comprising means for performing any of the embodiments as described in the appended claims.

Some embodiments of the invention are defined in the dependent claims.

BRIEF DESCRIPTION OF THE DRAWINGS

In the following, the invention will be described in greater detail with reference to the embodiments and the accompanying drawings, in which.

DETAILED DESCRIPTION

The following embodiments are exemplary. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments.

As said, there may be occasions where data needs to be broadcasted to many users simultaneously without a time consuming process of pairing. In such cases normal connections, which require pairing, may not be satisfactory. Therefore, there is proposed a radio device 100 as shown in FIG. 1.

Figure 1:
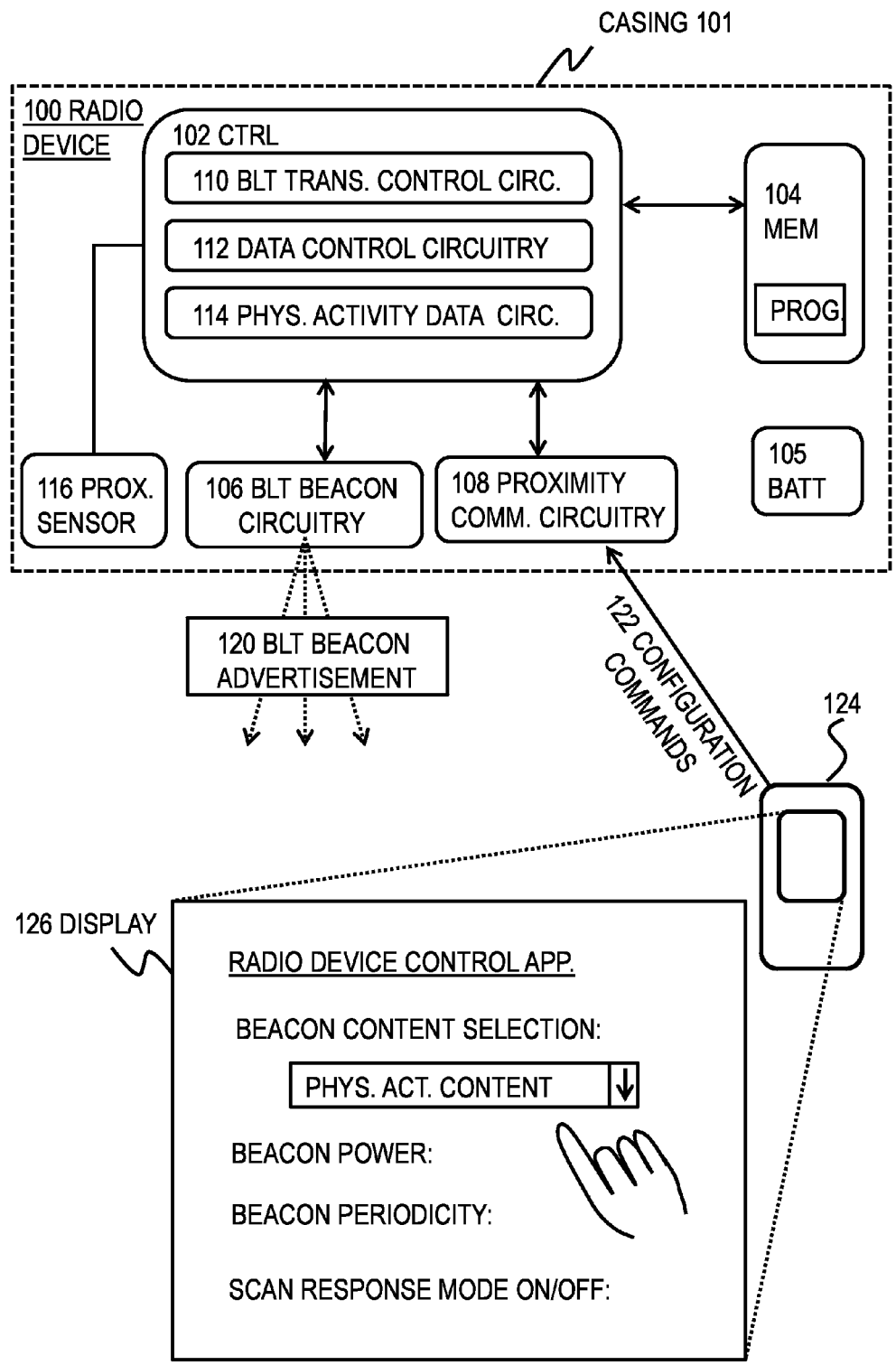
FIG. 1 presents a radio device, according to an embodiment.

The radio device 100, as shown in FIG. 1, may comprise a casing 101 surrounding and protecting the inside of the casing 101. The casing 101 may be made of plastic, for example. In an embodiment, the casing 101 may comprise attaching units for attaching the casing 101. These attaching units may be, e.g., apertures for screws, tape, glue, adhesive, sticker, rubber bands, etc. In an embodiment, the radio device 100 is a self-standing and self-operating device.

In an embodiment, the radio device 100 comprises a battery unit 105 for powering the radio device. The battery unit 105 may comprise rechargeable batteries, solar cells or some other means for generating power without external power supply, or any other type of battery capable for providing operation voltage to the radio device 100. However, in an embodiment, electric power is fed to the radio device 100 from a separate device so that the radio device 101 may not comprise the battery unit 105. In an embodiment, the separate device may be, e.g., a gym device which is coupled to the radio device via a wired bus. Further, in an embodiment, the radio device is integrated to another device, such as a training computer or a sensor, in which the battery of the respective device may provide power also for the radio device 100.

The radio device 101 may further comprise a Bluetooth beacon circuitry 106 for generating and advertising a Bluetooth (BLT) beacon signal 120 having frame format according to the Bluetooth standard. This may be for transmitting BLT advertisements to a plurality of devices within the BLT coverage area simultaneously. The BLT coverage area may be a few tens of meters, for example. The term BLT is used to represent all types of Bluetooth protocols and techniques, including the Bluetooth low energy (Bluetooth LE, BLE) or Bluetooth smart.

In an embodiment, to save the battery 105, the radio device 100 may comprise a motion detector (or other proximity sensor) to sense and alert the radio device 100 when someone is close to the radio device 100. The radio device 100 may, e.g., restrain from the beacon transmission when no-one is around to listen the beacon 120.

Transmission of the BLT beacon 120 may be advantageous as then many receivers may get the message at the same time. This may solve a number of local information sharing use cases. Let us imagine, for example, that many people are orienting. Each person is trying to find a number of check points for registering at each control. The radio device 100 may be implemented (e.g. attached via the attaching units) to each check point to transmit the BLT beacon 120 with a unique, check point-specific code. A mobile device carried by each person receives and registers the BLT beacon 120. This may be used at the end of the track as evidence to show that the person was in the vicinity of each check point. The mobile device may be a training computer, a smart phone, or any device a person may carry with him/her and capable of receiving the BLT beacon 120 (i.e. a Bluetooth capable device).

However, often data content and possibly transmission characteristics of the BLT beacon 120 transmission may need to changed. For example, using the same type of radio device 100 for different check points in the orientation example may require reconfiguring the data content of the beacon transmission 120. One radio device may need to advertise "Control point #1", whereas another radio device may be required to advertise "Control point #2".

It may be noted that the Bluetooth beacon signal 120 may initially comprise a pre-set data content and may initially be transmitted according to pre-set transmission settings. These pre-set content and settings may be set by the manufacturer of the radio device 100, for example. However, it may be that such reconfiguring of the transmission characteristics needs to be done in an ad-hoc manner, dynamically. Therefore, it may be too limiting to enable only the manufacturer of the radio device 100 to configure the settings of the beacon transmission 120. On the contrary, it may be advantageous for the end user to be able to reconfigure the BLT beacon 120 in an easy manner.

Therefore, the radio device 100 may also comprise a proximity communication circuitry 108 configured to receive configuration commands 122 wirelessly from a physically separate user device 124 over a magnetic induction-based proximity communication. The physically separate user device 124 may be a smart phone, for example. The smart phone 124 may comprise a specific application for giving the control commands, as shown on a display 126 of the smart phone 124. In an embodiment, the application may provide for drop-down menus for ease of selection. Such application may be downloadable from the Internet or pre-installed to the smart phone 124. The control commands 122 may be for programming or reconfiguring the radio device 100, as will be described.

In an embodiment the magnetic induction-based proximity communication applies near field communication (NFC). The near-field communication uses magnetic induction between two loop antennas located within each others near field. This may be advantageous for providing reliable and secure communication between the radio device 100 and the smart phone 124. In the NFC, the radio device 100 and the smart phone 124 may establish NFC communication by touching one device to another or by bringing the devices 100, 124 into proximity, usually no more than a few centimeters. In an embodiment, the NFC communication between the radio device 100 and the physically separate user device 124 is limited to ranges of less than 10 centimeters.

In an embodiment, the configuration commands 122 may not be given in other wireless means than over the magnetic induction-based proximity communication (e.g. the NFC). For example, receiving control commands 122 via a wireless local area network (WLAN) or via Bluetooth technology may not be possible. This may increase security of the radio device 100 as the radio device 100 may not be reconfigured by the control commands via an unknown remote device.

In yet one embodiment, the BLT beacon 120 is configured by using an Internet connection over Bluetooth (e.g. the BLE). Such internet connection may utilize wireless area network connections (such as a wireless personal area network, WPAN, or WLAN). An example protocol may be a 6LoWPAN protocol. The applied protocol may further apply a constrained application (COAP) protocol. In this case, there may be a wireless router that provides the possibility to send data to/from Internet.

In an embodiment, the user device 124 sending the control commands 124 may need to present a known identification to the radio device 100 before the radio device 100 accepts the control commands 122. This enhances the security of the radio device configuration. For example, each radio device 100 may have a unique identifier, which is given to the owner of the radio device 100 by the manufacturer, for example. Then the owner may set his smart phone 124 application to indicate this unique identifier along with the control commands 122. Then the radio device 100 receiving the indication of the unique identifier of the radio device 100 knows that the transmitter is an authorized transmitter. Consequently, the radio device 100 may accept and receive the transmitted control commands 122.

The radio device 100 may further comprise a control circuitry (CTRL) 102, such as at least one processor, and at least one memory 104 including a computer program code (FROG). The control circuitry 102 may comprise BLT transmission control circuitry 110 for controlling the transmission characteristics of the BLT beacon signal 120, and a data control circuitry 112 for controlling the data content of the BLT beacon signal 120.

Together the control circuitry 102, the memory 104 and the computer program code may cause the radio device 100 to perform specific operations. For example, the radio device 100 (or more particularly, the circuitries 110 and 112) may reconfigure at least part of the data content of the Bluetooth beacon signal 120 on the basis of the received configuration commands 122.

The configuration commands 122 may cause the data content of the Bluetooth beacon signal 120 to comprise at least physical activity related information. This information may, e.g., be related to physical activity data, such as heart activity or other physical activity sensor data, or it may be related to a physical activity session being performed or to-be-performed by at least one person carrying a device capable of receiving the BLT signal 120, to mention only a few possible options.

In a further embodiment, also transmission settings of the Bluetooth beacon signal 120 may be reconfigured on the basis of the received configuration commands 122.

In an embodiment, reconfiguration of the transmission settings may denote changing, on the basis of the configuration commands, the transmit power of the beacon 120. This may be needed if the coverage area of the beacon 120 is to be increased or decreased.

In an embodiment, reconfiguration of the transmission settings may denote changing, on the basis of the configuration commands, the beacon periodicity. For example, it may be advantageous to transmit the beacon more frequently in some scenarios than in others.

In an embodiment, reconfiguration of the transmission settings may denote changing, on the basis of the configuration commands, the frequency band of the beacon 120. For example, it may be advantageous to change the transmit channel depending on the surrounding devices or prevailing regulations. For example, some regions may have different regulations regarding the use of unlicensed industrial, scientific and medical (ISM) radio bands.

In an embodiment, reconfiguration of the transmission settings may denote setting, on the basis of the configuration commands, whether the data is encrypted or not. Encrypted data may be advantageous if the target group of devices does not include all devices in vicinity, but only some desired devices.

In an embodiment, reconfiguration of the transmission settings may denote setting, on the basis of the configuration commands, whether the radio device 100 operates in an advertisement mode only or whether the radio device 100 also transmits scan responses as a response to a reception of a scan request (i.e. a scan response mode). In an embodiment, in the advertisement mode the radio device 100 transmits certain data in the beacon 120 to all devices in the coverage area, whereas in the scan response mode, which may be used in addition to the advertisement mode, the radio device 100 transmit further data to only those devices which explicitly request for a scan response message.

In an embodiment, the beacon content may be divided into two categories. Firstly, the beacon content may comprise primary information that everybody in the coverage area may receive (i.e. the radio device 100 operating in the advertisement mode). The primary information may be, for example, the beacon type. Other possible information elements in the primary information may comprise at least one of the following: IEEE address (e.g. the medium access control, MAC, address), an identifier of the radio device 100 (such as a universally unique identifier, UUID), used transmit power (e.g. for enabling the receiver to determine the distance to the radio device on the basis of the transmit power and received signal strength indication, RSSI), advertisement packet structure (AD structure), and length of the beacon frame 120.

Secondly, beacon content may comprise scan response information. This information may be more detailed and devices interested in a particular radio device 100 may ask for this information from the radio device 100 via a beacon request message (i.e. the radio device 100 operates in the scan response mode). The scan response may comprise, for example, indication of the location of the radio device 100 and/or IEEE address.

Figure 2:
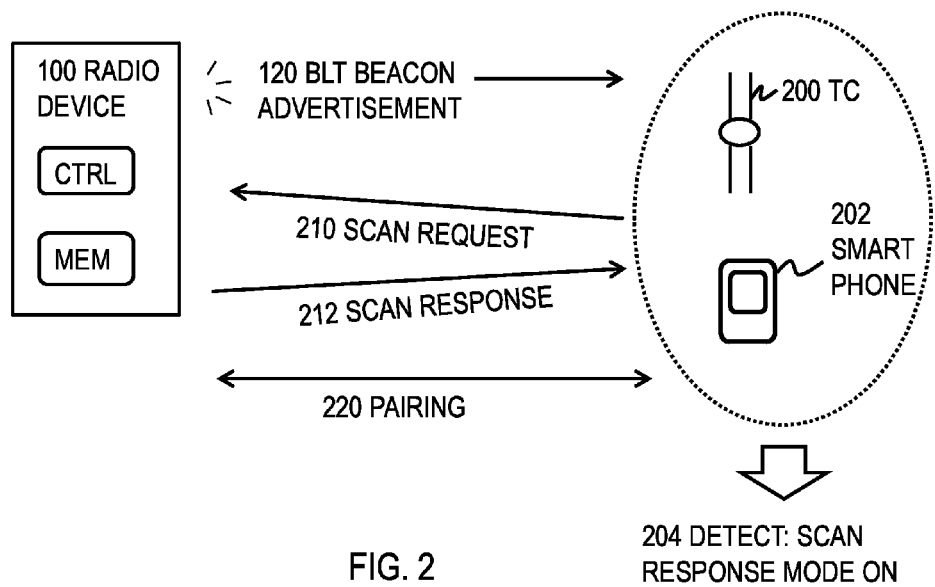
FIG. 2 shows a scan response mode of the radio device, according to an embodiment.

The use of such scan request/scan response negotiation is shown in FIG. 2, wherein the radio device 100 first transmits the beacon signal 120 to devices 200 (e.g. a training computer, TC) and 202 (e.g. a smart phone). After receiving the advertisement beacon 120, the receiving device (e.g. the device 200) may detect, in step 204, that the radio device 100 supports for the scan response mode. According to the scan response mode, the radio device 100 may respond with the scan response message, if requested by the device 200/202. Let us assume that the TC 200 then decides to ask for more information and transmit the scan request message 210. The radio device 100 receiving the scan request message 210 may then decide to respond with the scan response message 212 to the requesting TC 200. In this manner, the TC 200 may get more information of the radio device 100.

In an embodiment, the devices 100 and 200 (and/or 202) may further perform pairing 220, as shown in FIG. 2. In general, regarding pairing of two devices, such as two Bluetooth devices (e.g. the radio device 100 and the TC 200), the information transferred between the devices 100, 200 may be any data that the devices 100, 200 need to identify each other and to communicate with each other. The information may include, e.g., codes identifying the devices. The identifier may be a medium access control (MAC), or a part of a medium access control address. Bluetooth utilizes such MAC addresses, for example. A further requirement may be that the two devices 100 and 200 are in vicinity of each other. For Bluetooth pairing, the vicinity may be, e.g., a few tens of meters, such as less than hundred meters. After such process is successfully done between the two devices 100, 200, the devices 100, 200 may be called as paired devices and may transfer data between each other wirelessly.

Let us then look at reconfiguring the data content of the BLT beacon signal 1201 In an embodiment, reconfiguration of the data content of the beacon signal 120 may denote setting, on the basis of the configuration commands, the data content of the Bluetooth beacon signal to indicate a location dependent parameter with respect to a route traveled during the physical activity.

In an embodiment, the location dependent parameter may be a location of the radio device 100 on the route. This may correspond to the case where the radio device 100 advertises, e.g., "control point #1" during a physical activity of orientation.

In an embodiment, the location dependent parameter may be an altitude of the radio device 100 on the route. For example, during biking in mountains, there may be radio devices 100 disposed along the route. These locations may have also different altitude and the beacon signal 120 may broadcast the altitude so that people passing by may receive information of the altitude in their Bluetooth capable devices.

In an embodiment, the location dependent parameter indicates at least one of the following: distance run, distance left. For example, imagine a case where a person is running on a known track (such as during a marathon). There may be radio devices 100 placed out periodically along the track. Each radio device 100 broadcasts, for example, the distance run and/or the distance left to run in the beacon signal 120. When a runner passes by the radio device 100, he/she may automatically receive such location dependent parameter on his/her Bluetooth capable training computer, for example.

In one embodiment, the reconfiguration of the data content of the beacon signal 120 may denote setting, on the basis of the configuration commands, the data content of the Bluetooth beacon signal to indicate personal information related to the person carrying the radio device 100. Let us imagine a scenario in which a personal radio device 100 is used by a person running a marathon. When the person passes a control point, the control point may then register that this specific person has passed this known location of the control point. The personal radio device 100 may be integrated to the training computer 202, which the runner carries with him/her, for example.

Figure 3:
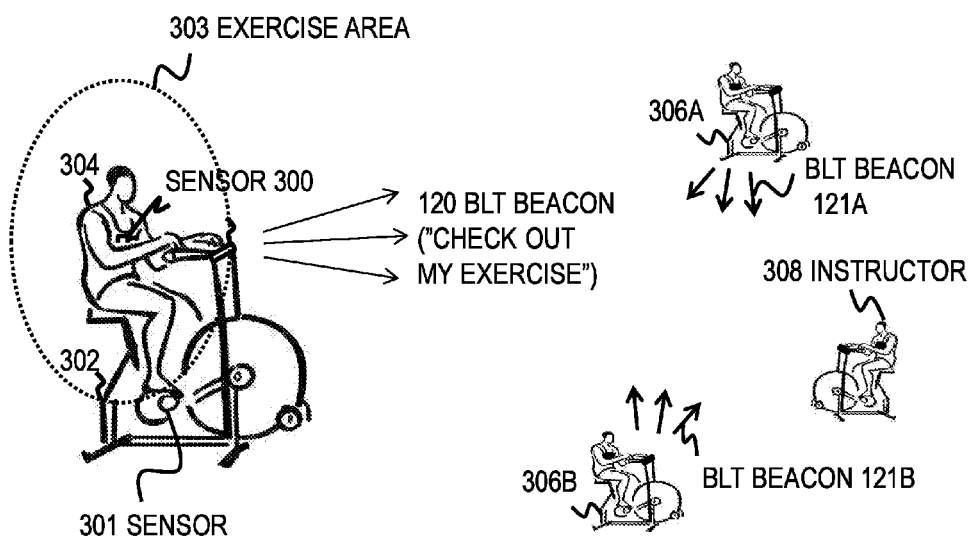
FIG. 3 shows an example of a use case of a beacon signal, according to an embodiment.

In an embodiment, as shown in FIG. 3, the radio device 100 is coupled to a physical activity sensor 300 measuring physical activity data of a person 304 performing a physical activity. In one embodiment, the radio device 100 may be integrated to the sensor device 300. In another embodiment, the radio device 100 is operatively coupled with the sensor 300. This may mean that the radio device 100 receives the physical activity data measured by the sensor 300 via a wireless or a wired interface.

Although FIG. 3 depicts a heart activity sensor as the sensor 300, the physical activity sensor 300 may be a sports/training computer having an integrated sensor (such as a GPS receiver), heart activity sensor (such as electrical or optical sensor to measure heart activity of the exerciser), electromyogram (EMG) sensor, a motion sensor (such as an accelerometer, a gyroscope, a stride sensor, a GPS receiver, a cadence sensor, and/or a magnetometer), a biochemical sensor (such as a lactate sensor, a blood sugar sensor and/or hormone sensor), for example. It may be noted that, for example, a GPS receiver or another motion sensor used for measuring speed and/or acceleration of the exercise, such as of running or skiing, may be classified as one type of physical activity sensor. It general, the physical activity sensor device may comprise any sensor or any other equipment capable of monitoring, storing and/or recording at least some physical activity data (exercise data) related to, associated with or applied during the physical activity.

The following is a non-limiting list of possible types of physical activity data obtained from at least one physical activity sensor or derived from the measured physical activity data: heart rate samples, heart rate variation samples, fat consumption, calorie consumption, activity samples, speed and/or pace samples, power samples, cadence samples, altitude samples, temperature samples, location samples, pedal index, left-right balance, running index, training load, galvanic skin response samples, fluid balance, skin temperature samples.

The physical activity may comprise intensive exercising or it may comprise, e.g. sleeping or other less intensive activity during which the activity is measured by the physical activity sensor (e.g. motions of the person may be recorded during the sleep by using at least one accelerometer, for example).

As said, the radio device 100 may be coupled to the physical activity sensor 300. Further, the control circuitry 102 of the radio device 100 may comprise a physical activity data circuitry 114, as shown in FIG. 1. This circuitry 114 may be responsible for acquiring (e.g. determining or receiving) a physical activity parameter on the basis of the measured physical activity data measured by the sensor 300. The physical activity parameter may be any parameter representing the measured physical activity data. For example, heart rate, calorie consumption, and/or distance elapsed may serve as the physical activity parameter. However, in an embodiment, the physical activity parameter is the physical activity data. The circuitry 114 may derive one or more physical activity parameters based on the physical activity data. For example, the circuitry 114 may derive heart rate and calorie consumption based on physical activity data measured by a single heart activity sensor.

In an embodiment, reconfiguration of the data content of the beacon signal 120 may denote setting, on the basis of the configuration commands, the data content of the Bluetooth beacon signal 120 to comprise the acquired physical activity parameter. This may allow other people to see the intensity of one's exercise. In an embodiment, the beacon signal 120 may also comprise advertisement information, such as "check out my data", so that other persons 306A, 306B, 308 in the coverage of the signal 120 may know to check out the physical activity parameter/data (e.g. the current heart rate or elapsed distance) from their own Bluetooth capable devices. This may increase social interacting in exercising groups, for example. It may be that the advertisement "check out my data" is sent in the advertisement beacon 120 which everybody may receive, whereas the actual physical activity parameter(s) is/are transmitted to only those who ask for it via the scan request/scan response messages. However, in another embodiment, the advertisement signal 120 already comprises the physical activity parameter(s).

In an embodiment, the advertisement signal 120 may also include an identifier of the transmitting radio device 100 (e.g. of the sensor/training computer). This identifier may be also set on the basis of the configuration commands 122. The identifier may be configured to indicate the name of the person 304, for example, so that other people 306A, 306B, 308 may know who is sending the physical activity parameter(s).

In an embodiment, a device of the person 308 (i.e. the instructor) may receive the physical activity parameter(s) over the beacon signals 120, 121A, 121B from many exercisers 304, 306A, 306B. The instructor's device's display may show all the device identifiers from which the Bluetooth beacon signals 120, 121A, 121B are received. Then the instructor 308 may select whose data the instructors wants to see. Alternatively, there may be a large display showing all exercisers' 304, 306A, 306B data simultaneously. Owing to the nature of the BLT advertisement signal 120, 121A, 121B, any person may see any person's physical activity parameter(s). In an embodiment, the person, whose data is being monitored, may not know this. This may act as motivator for performing well during the exercise. The instructor may check out if someone is not performing intensive training or if someone's heart rate is too high, for example.

In an embodiment, there is a sensor 301 integrated or otherwise coupled to the gym device 302. An example sensor type is a cadence sensor. The sensor 301 may be comprised in the radio device 100, or vice versa. Then, the radio device 100 comprising or operatively coupled to the sensor 301 may automatically transmit the advertisement 120 carrying the measured physical activity data.

In one embodiment, the radio device 100 may be coupled to a plurality of physical activity sensors 300 and 301. These sensors may comprise any sensors, such as a heart activity sensor and a cadence sensor (as is the case in FIG. 3). In such embodiment, the circuitry 114 may aggregate the physical activity data measured by the plurality of physical activity sensors 300, 301. The aggregation may denote compiling one packet including many types of physical activity data. In one embodiment, the aggregation may mean applying many types of physical activity data to derive one physical activity parameter. For example, deriving a running index may require information from a motion sensor (e.g. a GPS receiver) and from a heart activity sensor.

In an embodiment, reconfiguration of the data content of the beacon signal 120 may denote setting, on the basis of the configuration commands, the data content of the Bluetooth beacon signal 120 to comprise the aggregated physical activity data. This option may allow for more detailed and compact packet to be received by others.

Figure 4:
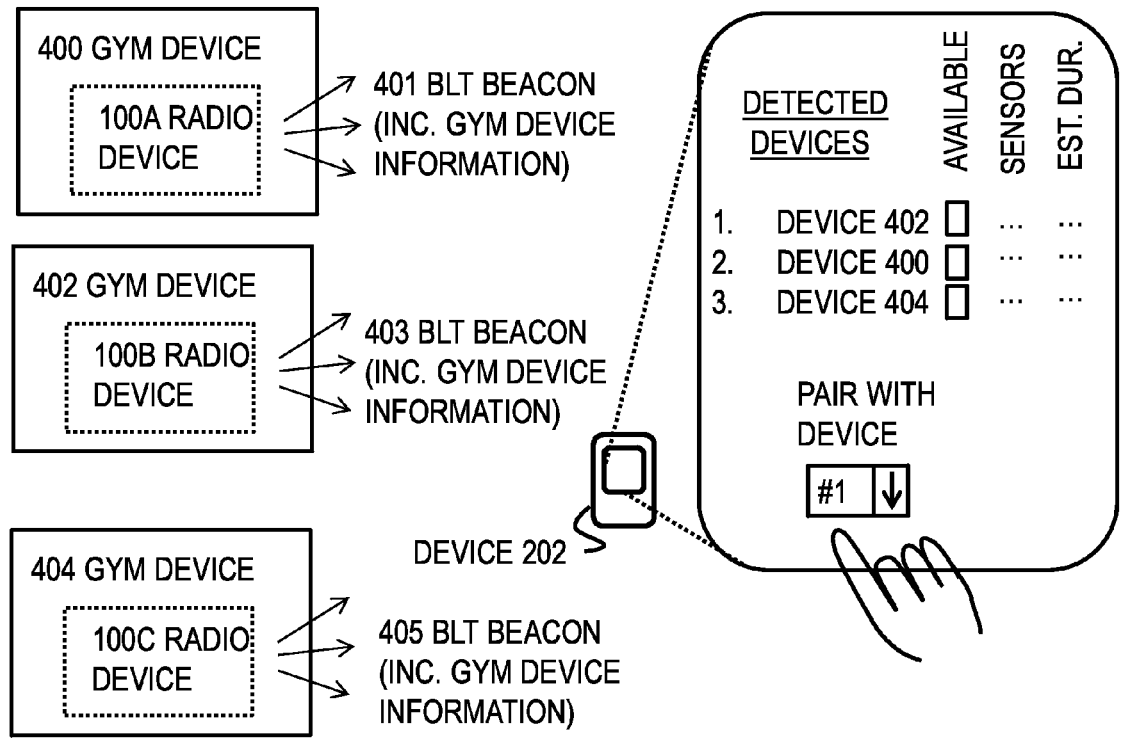
FIG. 4 shows an example of a use case of the beacon signal, according to an embodiment.

Let us then imagine that a person carrying a smart phone 202 or a smart watch with Bluetooth capability enters a gym, as illustrated in FIG. 4. Let us further assume that radio devices 100A, 100B, 100C transmitting Bluetooth beacons 401, 403, 405 may be coupled to gym devices, such as a strength training device 400, a bicycle 402, and a treadmill 404. The radio device 100A, 100B, and 100C are similar to the radio device 100. The person scans the environment using the BLT capable smart phone 202 to find all the available beacon signals 401, 403, and 405, corresponding to gym devices 400, 402, 404.

In this embodiment, reconfiguration of the data content of the beacon signals 401, 403, 305 may denote setting, on the basis of the configuration commands 122, the data content of the Bluetooth beacon signals 401, 403, 305 to indicate information specific to the said gym devices. For example, the beacon 401 from the radio device 100A may advertise the name of the corresponding gym device 401, e.g., a biceps training device.

In an embodiment, the radio devices 100A, 100B, 100C may comprise a proximity sensor 116 (shown in FIG. 1) for sensing whether or not someone is in an exercise area of the gym device. Each gym device may have a specific exercise area comprising the area in proximity of the relevant gym device. Such exercise area is typically dedicated to a specific exercise and may involve the use of exercise equipment. The exercise area may be an area dedicated to an individual during the exercise. In this sense, the exercise area may also be called a personal exercise area. The exercise area may be defined by the type of exercise to be carried out in the exercise area and/or by the type of the relevant gym device, such as a treadmill, bike, or cross-training equipment. The dimensions of the personal exercise area may be such that the person is expected to stay within the bounds of the personal exercise area during the exercise. The range of the exercise area may be, for example, 1×1 meters or 1×2 meters. For example, in case of a treadmill, the exercise area may correspond to the area above the moving mat in which the user runs. In case of a bicycle 302, as shown in FIG. 3, the exercise area 303 may comprise the area above the seat of the bicycle. In case of weight lifting, the exercise area may comprise the area in which the specific weight lifting by the user occurs. It should be noted though that in the case the user performs push-ups, squats, or alike, on a mat or on a floor, the exercise area may be the area in which the exerciser performs the push-ups or alike. In this case, there may not be any specific gym device with which the exercise is performed. However, even in such case there may be the radio device 100 located near that exercise area in order for the radio apparatus 100 to detect the presence of an exerciser in the exercise area. Further, in addition to proximity limitations, the exercise area may also have angular limitations so that the exercise area is present only in one predetermined direction with respect to the gym device. For example, in case of the bicycle 302, the proximity area in front of the bicycle may not be part of the exercise area 303. In other words, the exercise area is the area in which the user is expected to be while performing the exercise with the corresponding gym device. The exercise area may be empirically derived for each type of gym device.

In an embodiment, the information specific to the gym device (e.g. the gym device 402) may indicate whether the corresponding gym device 400, 402, 404 is available or not on the basis of whether someone is detected to be in the exercise area of that gym device. This may aid the person entering the gym to select a suitable and available gym device for him/her simply by looking at the display screen of the device 202. The display may for example show all available devices in green, and all the non-available devices in red.

In an embodiment, it may be indicated in the beacon signals 401, 403, 405 how long the current exerciser has used the gym device and possibly also estimate the remaining time duration the person will spend in the gym device. The estimation may be based on empirical data relating to the use of different type of gym devices. In one embodiment, the estimation may be based on information input by the current exerciser to the gym device 402. For example, the current exerciser may have set the exercise duration in the beginning of the exercise, such as 30 minutes bicycling. This input information may be acquired by the radio device 100B as the radio device 100B may be operatively coupled to the gym device 402. Therefore, any information of the physical activity session and any information input by the exerciser or obtained from the exercise (such as personal credentials obtained wirelessly from the user device) may be readily available also to the control circuit 102 of the radio device 100. In an embodiment, the estimation is based on comparison between training plan parameters, such as workout repetitions or time spent on cardiac zone, and the measurement corresponding to training plan parameters that characterize the progress of the workout.

In one embodiment, the information specific to the gym device (e.g. to the gym device 402 comprises at least physical activity sensors coupled to the gym device 402. For example, the gym device 402 may comprise an in-built cadence sensor 301 (as shown in FIG. 3). Then, the user may readily from his/her screen see which sensors are available in each gym device 400, 402, 404. If the person wants detailed exercise analysis, then he/she may be likely to select a gym device with suitable exercise sensors.

In an embodiment, the information specific to the gym device (e.g. the gym device 402 comprises at least the available weights of the strength training gym device 400. The information regarding the available weights may be input to the radio device 100A via the configuration commands 122.

The division between what information is transmitted in the open-to-everybody advertisement 120 and what information is included only in the scan response may be implementation specific and reconfigurable via the configuration commands 122.

As shown in FIG. 4, the device 202 may then lists the gym devices 400, 402, 404 in an order according to a predetermined criteria (such as signal strength, type of the gym device, whether someone is using the gym device currently, presence of certain sensor, etc.). Thereafter, the person may decide to pair with a suitable device, e.g. with the gym device 402, as shown in FIG. 4. When the gym device 402 is connected to the smart phone 202, the user may be prompted to give his consent in order to share his/her personal data stored in the smart phone 202. Once agreed, the gym device 402 may automatically be configured with his/her personal data (e.g. weight, height, heart rate max). This information may, as said, be available also to the radio device 1006 coupled to the gym device 402. The smart phone 202 may then be ready to receive data from the selected gym device 402. As the exercise is over, the user may release the connection from the gym device 402 or from the phone 202.

In the example of FIG. 4, the radio devices 100A-100C may be coupled to gym devices 400, 402, 404. In an embodiment the coupling may denote that the radio device (e.g. the radio device 100A) is integrated into the gym device 400.

Figure 5:
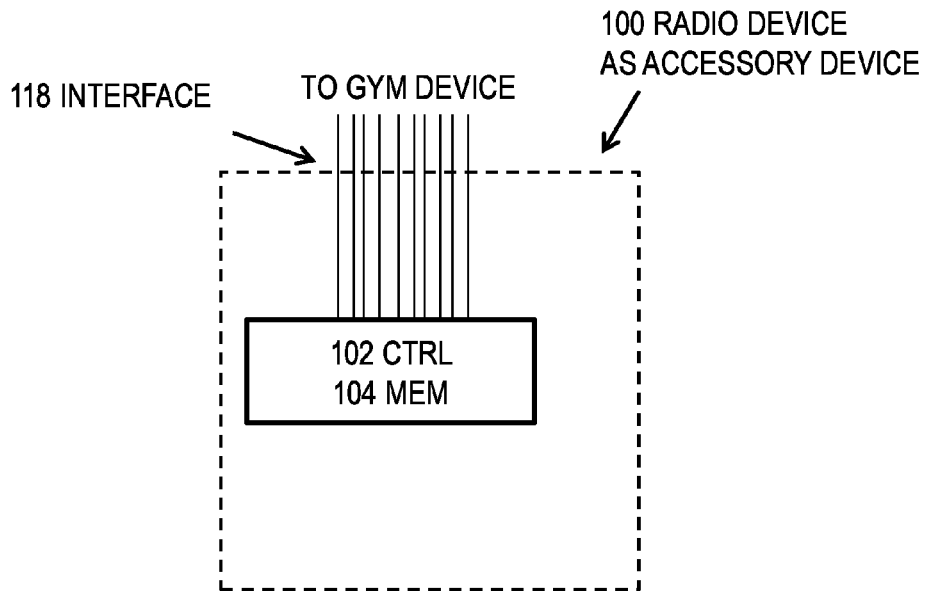
FIG. 5 depicts the use of the radio device as an accessory device, according to an embodiment.

In another embodiment, as shown in FIG. 5, the radio device 100 comprises a wired bus interface 118 for releasably attaching the radio device to a gym device. By releasable attachment it is meant that any person may attach the radio device 100 detachably and/or remove the radio device 100 from the corresponding gym device. This may enable the radio device 100 to act as an accessory device. The gym device may comprise a mounting location or a docking station, such as a socket or a recession, to receive and support the radio device 100 during the physical exercise. Such docking station may comprise an electric connector for connecting electronic circuitries of the gym device to the wired bus interface 118 of the radio device 100. This embodiment may allow the exerciser to share his/her exercise to other people in the area even if the gym device itself is not configured or capable to transmit the Bluetooth beacon signal 120

The wired bus 118 and the interface of the gym device may be used to convey, e.g. the physical activity data measured by the integrated sensors 301 of the gym device and physical activity data derived by the gym device (such as calorie consumption). In an embodiment, the radio device 100 may further receive physical activity data from the paired user device (e.g. a training computer and/or at least one sensor). As the radio device 100 may in this manner gather the physical activity data related to the physical activity session from many sources, the radio device 100 may then possibly aggregate the data, possibly derive at least one physical activity parameter representing the physical activity data, and then transmit the Bluetooth beacon signal 120.

In those embodiments where the radio device 100 is coupled (e.g. integrated) to a gym device, the gym device and the radio device 100 may be seen as one entity where information sharing between the gym device and the radio device 100 may take place.

In an embodiment, the radio device 100 does not comprise a user interface. That is the radio device 100 may not provide a possibility for programming the beacon transmission via the device itself. However, the programming via the NFC, as explained above, is possible. This may produce savings in manufacturing expenses and provide increased security of the radio device 100.

However, in another embodiment, the radio device 100 may comprise a user interface comprising, for example, at least one keypad, a microphone, a touch display, a display, a speaker, etc. The user interface may be used to control and reconfigure the radio device 100 by the user.

Figure 6:
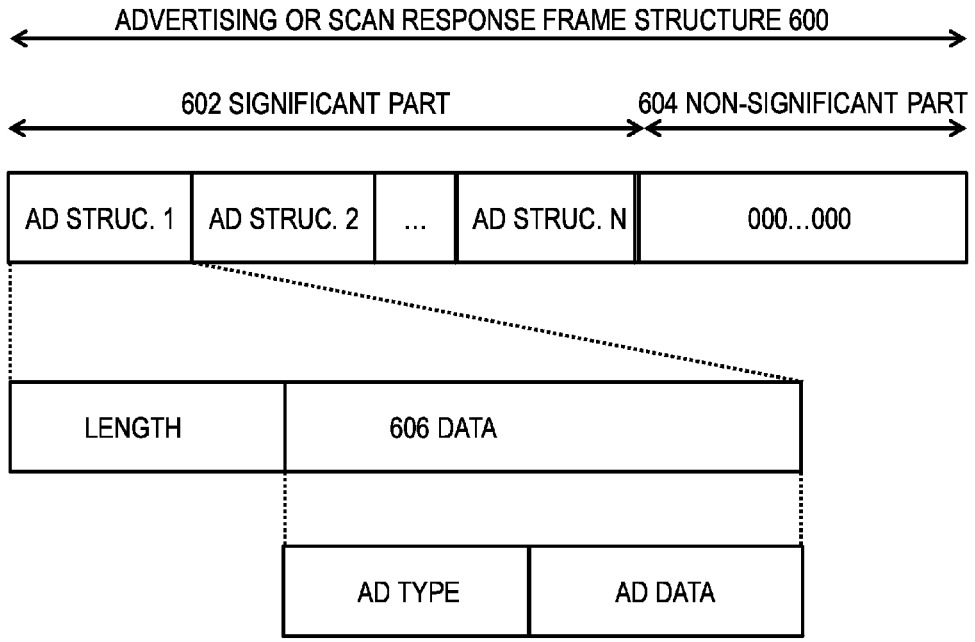
FIG. 6 depicts a frame format of the beacon signal, according to an embodiment.

FIG. 6 shows a frame structure 600 of the beacon signal 120, or of the scan response signal 212 of FIG. 2. The frame is divided into a significant part 602 and into a non-significant part 604. The significant part 602 may comprise the advertising structures (AD structure) 1, 2, . . . , N, each having a certain length and payload data 606. The payload data 606 may then comprise the advertising (AD) type and advertising data-parts. These AD data parts may carry the information that the radio device 100 wished to advertise to receivers in the coverage area via the beacon signal 120.

In an embodiment, the radio device 100 may operate in a central role of the Bluetooth protocol and the surrounding device receiving the beacon 120 may operate in the slave (peripheral) role of the Bluetooth protocol.

In another embodiment, the radio device 100 may operate in the peripheral role of the Bluetooth protocol and the surrounding device receiving the beacon 120 may operate in the central role of the Bluetooth protocol.

In an embodiment, the applied Bluetooth protocol may be based on generic access profile (GAP), which may define how two Bluetooth devices discover and establish a connection with each other. The GAP profile may apply the central and peripheral roles in the communication. For example, a radio device 100 coupled to a gym device may be a GAP Central and a GAP Broadcaster at the same time, so while the radio device 100 device scans for other devices in vicinity, the radio device 100 also broadcasts (non-connectable advertisement) the beacon 120 including, e.g. the name and type of the coupled gym device (as programmed with the configuration commands 122). The smart phone or other training computer carried by a user may be a GAP Peripheral and GAP observer. The user device may start to send directed connectable advertisement to that particular gym device for pairing, once the user selects the desired gym device from his/her device (as explained above).

In an embodiment, the radio device 100 of the gym device may thus wirelessly receive a connection request from a Bluetooth capable user device (e.g. the training computer or a smart phone). The connection request may comprise needed information for the radio device 100 to pair with the user device. In addition, the connection request may also comprise required information for pairing with at least one Bluetooth capable physical activity sensor of the user. This may be advantageous when a person carries the smart phone and at least one sensor, such as a BLT capable heart activity sensor. It may be beneficial for the gym device (comprising the radio device 100) to pair also with the at least one sensor in order to receive measured physical activity data from the sensor and, possibly, display the data to the user via a display of the gym device. Thus, the radio device 100 may further connect to the Bluetooth capable user device and to the at least one Bluetooth capable physical activity sensor.

As one possible advantage, the proposed beacon transmission 120 allows many devices in the coverage area of the beacon transmission 120 to receive information without pairing (i.e. without setting up a dedicated connection between the devices). As such, the radio device 100 may, as a default, apply a non-connected advertising mode. However, as explained above, there may be cases that result in pairing between the devices.

Figure 7:
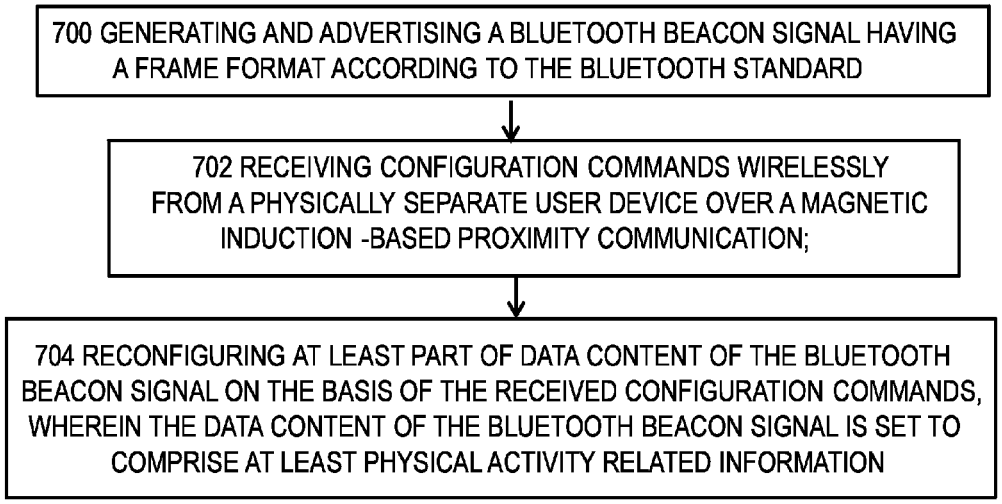
FIG. 7 shows a method, according to an embodiment.

FIG. 7 discloses a method, comprising, in step 700, generating and advertising, by a radio device 100, the Bluetooth beacon signal 120 having a frame format according to the Bluetooth standard. In step 702, the method comprises receiving configuration commands 122 wirelessly from a physically separate user device 124 over a magnetic induction-based proximity communication, such as the NFC. In step 704, the method comprises reconfiguring at least part of data content of the Bluetooth beacon signal 120 on the basis of the received configuration commands 122, wherein the data content of the Bluetooth beacon signal 120 is set to comprise at least physical activity related information.

In an embodiment, there is provided a system comprising the radio device 100 and a physical activity device (e.g. a smart phone, a training computer, or a physical activity sensor). The physical activity sensor may receive the Bluetooth beacon signal 120 from the radio device 100 and transmit, based on user instructions, a connection request to the radio device 100.

In one embodiment, the radio device 100 is comprised in a gym device and the data content of the Bluetooth beacon signal 120 comprises information specific to the gym device. In such case, the physical activity device may list the plurality of gym devices on the basis of the received at least one Bluetooth beacon signal 120. As indicated earlier, there may be a pre-set criterion for arranging the gym devices in the list.

In an embodiment, there is provided the user device 124 comprising a software program for setting, based on user instructions, control commands 122 to be transmitted to the radio device 100. The transmission may take place via the NFC, as explained above.

Although not shown, the radio device 100 may further comprise communication interface (TRX) comprising hardware and/or software for realizing communication connectivity according to one or more communication protocols, such as cellular or WLAN communication. The TRX may provide the apparatus with communication capabilities to access the radio network, for example. In an embodiment, the radio device 100 may transmit the physical activity data to a web-based service located in a server of a network. The web service may comprise exercise data user accounts (UA), each exercise data user account comprising exercise data associated with a specific user. As such, there may be different user accounts for different users #1, #2, . . . , and #N. An example of such a web service 106 may be a Polar Personal Trainer (PPT), Polar Flow or iFIT service which comprises a database for storing the plurality of user accounts. It should be noted that the user accounts may be stored on a same or on different server computers. The radio device 100 may also receive through the Bluetooth communication personal information from the person associated with the paired user device. This may be for identifying the user account in the service of the network.

As used in this application, the term 'circuitry' refers to all of the following: (a) hardware-only circuit implementations, such as implementations in only analog and/or digital circuitry, and (b) combinations of circuits and soft-ware (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware. The term 'circuitry' would also cover, for example and if applicable to the particular element, a baseband integrated circuit or applications processor integrated circuit for a mobile phone or a similar integrated circuit in a server, a cellular network device, or another network device.

The techniques and methods described herein may be implemented by various means. For example, these techniques may be implemented in hardware (one or more devices), firmware (one or more devices), software (one or more modules), or combinations thereof. For a hardware implementation, the apparatus(es) of embodiments may be implemented within one or more application-specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. For firmware or software, the implementation can be carried out through modules of at least one chip set (e.g. procedures, functions, and so on) that perform the functions described herein. The software codes may be stored in a memory unit and executed by processors. The memory unit may be implemented within the processor or externally to the processor. In the latter case, it can be communicatively coupled to the processor via various means, as is known in the art. Additionally, the components of the systems described herein may be rearranged and/or complemented by additional components in order to facilitate the achievements of the various aspects, etc., described with regard thereto, and they are not limited to the precise configurations set forth in the given figures, as will be appreciated by one skilled in the art.

Embodiments as described may also be carried out in the form of a computer process defined by a computer program. The computer program may be in source code form, object code form, or in some intermediate form, and it may be stored in some sort of carrier, which may be any entity or device capable of carrying the program. For example, the computer program may be stored on a computer program distribution medium readable by a computer or a processor. The computer program medium may be, for example but not limited to, a record medium, computer memory, read-only memory, electrical carrier signal, telecommunications signal, and software distribution package, for example. Coding of software for carrying out the embodiments as shown and described is well within the scope of a person of ordinary skill in the art.

Even though the invention has been described above with reference to an example according to the accompanying drawings, it is clear that the invention is not restricted thereto but can be modified in several ways within the scope of the appended claims. Therefore, all words and expressions should be interpreted broadly and they are intended to illustrate, not to restrict, the embodiment. It will be obvious to a person skilled in the art that, as technology advances, the inventive concept can be implemented in various ways. Further, it is clear to a person skilled in the art that the described embodiments may, but are not required to, be combined with other embodiments in various ways.

What is claimed is:

1. A radio device, comprising:
a Bluetooth circuitry configured to generate and advertise a Bluetooth beacon signal having a frame format according to the Bluetooth standard;
a proximity communication circuitry configured to receive configuration commands wirelessly from a physically separate user device over a magnetic induction-based proximity communication; and
at least one processor and at least one memory including a computer program code, wherein the at least one memory and the computer program code are configured, with the at least one processor, to cause the radio device to perform operations comprising reconfiguring physical activity information associated with a physical activity session performed by a user, which is at least part of data content of the Bluetooth beacon signal, on the basis of the received configuration commands.

2. The radio device of claim 1, wherein the magnetic induction-based proximity communication applies near field communication (NFC).

3. The radio device of claim 1, wherein the radio device is further caused to perform operations comprising reconfiguring at least part of transmission settings of the Bluetooth beacon signal on the basis of the received configuration commands.

4. The radio device of claim 1, wherein the radio device is further caused to perform operations comprising setting, on the basis of the configuration commands, the data content of the Bluetooth beacon signal to indicate a location dependent parameter with respect to a route traveled during a physical activity.

5. The radio device of claim 4, wherein the location dependent parameter indicates at least one of altitude, distance run, distance left.

6. A radio device coupled to a physical activity sensor measuring physical activity data of a person performing a physical activity, the radio device comprising:
a Bluetooth circuitry configured to generate and advertise a Bluetooth beacon signal having a frame format according to the Bluetooth standard;
a proximity communication circuitry configured to receive configuration commands wirelessly from a physically separate user device over a magnetic induction-based proximity communication; and
at least one processor and at least one memory including a computer program code, wherein the at least one memory and the computer program code are configured, with the at least one processor, to cause the radio device to perform operations comprising:
acquiring at least one physical activity parameter on the basis of the measured physical activity data; and
reconfiguring physical activity parameter information associated with a physical activity session performed by a user, which is at least part of data content of the Bluetooth beacon signal on the basis of the received configuration commands.

7. A radio device coupled to a plurality of physical activity sensors, the radio device comprising:
a Bluetooth circuitry configured to generate and advertise a Bluetooth beacon signal having a frame format according to the Bluetooth standard;
a proximity communication circuitry configured to receive configuration commands wirelessly from a physically separate user device over a magnetic induction-based proximity communication; and at least one processor and at least one memory including a computer program code, wherein the at least one memory and the computer program code are configured, with the at least one processor, to cause the radio device to perform operations comprising:

aggregating physical activity data measured by the plurality of physical activity sensors; and reconfiguring aggregated physical activity data associated with a physical activity session performed by a user, which is at least part of data content of the Bluetooth beacon signal on the basis of the received configuration commands.

8. A radio device coupled to a gym device, the radio device comprising:

a Bluetooth circuitry configured to generate and advertise a Bluetooth beacon signal having a frame format according to the Bluetooth standard;

a proximity communication circuitry configured to receive configuration commands wirelessly from a physically separate user device over a magnetic induction-based proximity communication; and at least one processor and at least one memory including a computer program code, wherein the at least one memory and the computer program code are configured, with the at least one processor, to cause the radio device to perform operations comprising reconfiguring physical activity information associated with a physical activity session performed by a user, which is at least part of data content of the Bluetooth beacon signal on the basis of the received configuration commands, wherein the data content of the Bluetooth beacon signal is set to comprise information that is specific to said gym device.

9. The radio device of claim 8, wherein the information specific to the gym device is configured to comprise information about at least physical activity sensors coupled to the gym device.

10. The radio device of claim 8, wherein the radio device further comprises a proximity sensor configured to sense whether or not someone is in a gym device-specific exercise area of the gym device, and wherein the information specific to the said gym device is configured to indicate whether the said gym device is available or not on the basis of whether someone is detected to be in the gym device-specific exercise area.

11. The radio device of claim 8, wherein the radio device is further caused to perform operations comprising estimating time duration the current exerciser of the gym device will use the gym device, and wherein the information specific to the said gym device is configured to indicate the estimated time duration.

12. The radio device of claim 8, wherein the radio device comprises a wired bus interface for releasably attaching the radio device to the gym device.

13. A method, comprising:

generating and advertising a Bluetooth beacon signal having a frame format according to the Bluetooth standard;

receiving configuration commands wirelessly from a physically separate user device over a magnetic induction-based proximity communication; and reconfiguring physical activity related information associated with a physical activity session performed by a user, which is at least part of data content of the Bluetooth beacon signal on the basis of the received configuration commands.

14. A computer program product embodied on a non-transitory distribution medium readable storing instructions that, when executed by an apparatus, perform a method comprising:

generating and advertising a Bluetooth beacon signal having a frame format according to the Bluetooth standard;

receiving configuration commands wirelessly from a physically separate user device over a magnetic induction-based proximity communication; and reconfiguring physical activity related information associated with a physical activity session performed by a user, which is at least part of data content of the Bluetooth beacon signal on the basis of the received configuration commands.

15. A radio device, comprising:

a Bluetooth circuitry configured to generate and advertise a Bluetooth beacon signal having a frame format according to the Bluetooth standard;

a proximity communication circuitry configured to receive configuration commands wirelessly from a physically separate user device over a magnetic induction-based proximity communication; and at least one processor and at least one memory including a computer program code, wherein the at least one memory and the computer program code are configured, with the at least one processor, to cause the radio device to perform operations comprising setting, on the basis of the configuration commands, whether the radio device operates in an advertisement mode only or whether the radio device also transmits scan responses as a response to a reception of a scan request, and the processor reconfiguring physical activity information associated with a physical activity session performed by a user, which is at least part of data content of the Bluetooth beacon signal on the basis of the configuration commands.

16. The radio device of claim 15, wherein the radio device is further caused to perform operations comprising:

indicating, on the basis of the configuration commands, in at least part of the data content of the Bluetooth beacon signal that the radio device also transmits scan responses as a response to a reception of a scan request;

receiving a scan request from the user device; and transmitting a scan response to the user device as a response to receiving the scan request.

* * * * *

UNITED STATES PATENT AND TRADEMARK OFFICE
CERTIFICATE OF CORRECTION

PATENT NO. : 9,763,056 B2  
APPLICATION NO. : 14/319754  
DATED : September 12, 2017  
INVENTOR(S) : Raphael Ansermet, Niclas Granqvist and Markku Karjalainen Page 1 of 1

It is certified that error appears in the above-identified patent and that said Letters Patent is hereby corrected as shown below:

In the Abstract:  
Now reads: "…pro-gram…"  
Should read: -- …program… --

Signed and Sealed this  
Third Day of April, 2018

Andrei Iancu  
*Director of the United States Patent and Trademark Office*